5/1/84 XR 4,446,395

United States Patent [19]

Hadjicostis

[11] 4,446,395

[45] May 1, 1984

[54] SHORT RING DOWN, ULTRASONIC TRANSDUCER SUITABLE FOR MEDICAL APPLICATIONS

[75] Inventor: Andreas Hadjicostis, North Brunswick, N.J.

[73] Assignee: Technicare Corporation, Solon, Ohio

[21] Appl. No.: 335,920

[22] Filed: Dec. 30, 1981

[51] Int. Cl.[3] ........................ H01L 41/08; A61B 10/00

[52] U.S. Cl. .................................... 310/327; 310/334; 310/336; 128/660

[58] Field of Search ................................ 128/660-663; 73/632, 644; 310/326, 334-336

[56] References Cited

U.S. PATENT DOCUMENTS 4,101,795 7/1978 Fukumoto et al. ................. 310/336
4,240,003 12/1980 Larson ................................ 310/326
4,277,711 7/1981 Hanafy ............................ 310/336 X

*Primary Examiner*—William E. Kamm
*Assistant Examiner*—Francis J. Jaworski

[57] ABSTRACT

A highly efficient piezoelectric transducer suitable for medical applications is disclosed which exhibits a 40 db ring down time of less than 3 cycles, that is, of less than 0.7 microsecond at 4.2 MHz. The subject transducer comprises a single crystal lithium niobate active element which is supported on a formed backing material which is lapped to a surface flatness of better than 0.0002 inches (0.0015 cm). The subject transducer, which is designed to be driven at 4.2 MHz further comprises a first matching layer having an impedance of $6.8\text{-}7.4\times10^6$ kg/m$^2$ sec and a second matching layer having an impedance of between $1.8\text{-}2.4\times10^6$ kg/m$^2$ sec. An alternate embodiment dual-power transducer is also disclosed which is suitable for operating at different power levels to selectively image or produce lesions in selected body tissues.

21 Claims, 6 Drawing Figures

SHORT RING DOWN, ULTRASONIC TRANSDUCER SUITABLE FOR MEDICAL APPLICATIONS

CROSS-REFERENCE TO RELATED APPLICATIONS

This application is related to the co-pending application of David Vilkomerson entitled "Method And Apparatus For Imaging And Thermally Scarring Varicose Veins Using Ultrasound", Ser. No. 337,795 filed Jan. 7, 1982, which application is hereby incorporated by reference as if fully set forth herein.

BACKGROUND OF THE INVENTION

The present invention relates to the field of large aperture ultrasonic transducers, and more particularly to transducers which are useful in ultrasonic imaging systems for imaging internal body tissues and for other related medical applications.

In the field of ultrasonic medical imaging, it has long been desired to achieve good lateral resolution, good penetration, good axial resolution, reasonable electrical impedance characteristics, and sufficient ruggedness to permit extended transducer use. Unfortunately, optimization of certain of the forementioned characteristics tends to prevent optimization of certain other characteristics which may be deemed necessary or desirable for a given application. For example, the degree of lateral resolution (d) which is possible using a transducer is defined by the Rayleigh criterion as being inversely proportional to aperture size (a), and directly proportional to the focal length of the optical system and the wave length of the radiation involved. Accordingly, in the field of medical imaging, where good lateral resolution is preferred, and where trapezoidal images are to be avoided during sector scanning, relatively large apertures (e.g., greater than 1.5 inches (3.8 cm) and, on the order of about 3 inches (7.6 cm)) are desired. At the same time, it is often difficult to achieve the short impulse response which is required to achieve good axial resolution. In the absence of short impulse responses, reflected pulses from neighboring but distinct tissues tend to overlap due to the long train of oscillations (long ring down time) associated with long impulse responses. Since resolution is directly proportional to wave length, to some degree resolution can be increased at higher transducer frequencies, however, higher frequencies are not as effective at penetrating body tissue, tend to cause shadowing effects within those tissues and require much higher sensitivities in order to effectively image deep lying tissues without having to use high intensity ultrasound. In optimizing each of the above-mentioned parameters, it is further necessary to insure that the resulting transducer exhibits a reasonable electrical impedance which enables the transducer to be matched to a driving source without undue effort.

In recent years, various large aperture transducers suitable for medical applications have been suggested, several of which have achieved a certain degree of commercial success. In "Transducer Arrays Suitable For Acoustic Imaging", by C. S. DeSillets, G.L. Report No. 2833, Stanford University, California (1978) a relatively small apertured transducer is disclosed having a lead metaniobate active element. DeSillets' transducer is air backed, is designed for operation at 2.06 MHz, exhibits a real impedance at $f_o$ of 64 ohms, and exhibits a round trip loss of 6.5 dB. Using a ¼ wave length matching layer of DER 332 epoxy, this transducer exhibits an estimated ring down time to 40 dB of about 3.25 microseconds.

More recently, large aperture transducers have been suggested which exhibit comparable or better ring down times than the aforementioned DeSillets' transducer. Such transducers have typically featured piezoelectric materials exhibiting good electromechanical couplings (high $k^{2T}$ values) and suitable dielectric contants for their intended applications. Presently available piezoelectric materials have coupling coefficients ($k^{2T}$) in the range of 0.02 for PVDF to 0.26 (for PZT-4). Lead metaniobate active elements similar to that disclosed by DeSillets exhibit $k^{2T}$ values in the 0.122 to 0.144 range. These materials, however, have either too low a coupling coefficient or too high a dielectric constant and are thus unsuitable for large aperture transducers.

Lithium niobate is the presently preferred material for use in large cross-section transducers. Lithium niobate has been typically used as the active element in transducers used for SAW (surface acoustic wave) applications, and more recently has been used as the active element in ultrasound imaging transducers. In one such transducer, a lithium niobate active element having a thickness of about 1.05 mm, and designed to operate at 3.2 MHz was utilized in a transducer having an impregnated epoxy backing and two matching layers having impedances of 10.6 and 3.1 kg/m$^2$ sec. Such transducers were typically able to achieve ring down times to 40 dB in the range of 1.4 to 1.7 microseconds.

One method which has been employed by the art in designing ultrasonic transducers is the use of computer modeling programs which are based on acoustic theory and which attempt to predict the theoretical performance of tranducers which are constructed from various active elements and various matching materials. Such approaches at optimizing transducer performance have been described in papers by G. Kino, et al such as the paper entitled "The Design of Broadband and Efficient Acoustic Wave Transducers", presented at the IEEE Conference on Sonics and Ultrasonics (1980). Such programs generally take into account transducer impedance, matching layer thickness, backing properties, etc. for the purpose of optimizing transducer performance. The application of such programs has caused the substantial improvement in such parameters as ring down. For example, in one experiment conducted at Stanford University (as reported in the above paper) wherein a transducer was constructed in accordance with computer modeling theories, a 3.5 MHz transducer, 2 mm in diameter, was improved in ring down from 15 to 5 cycles.

Notwithstanding the theoretical advances in this area, the prior art has yet to achieve a transducer exhibiting a round trip 40 dB ring down time of less than 1 microsecond at 4.2 MHz. In this regard, applicant has recently tested an ECHO transducer E81X414 (3.5 MHz) to determine its round trip loss and 40 dB ring down time. This transducer was tested by generating a tone burst in the transducer of about 10 cycles in duration having an amplitude of 10–15 volts. This tone burst was transmitted through water reflecting it off a stainless steel plate and measuring the amplitude of the return pulse as well as the time it takes for the return pulse to decay down 40 dB from the last maximum. This test is conducted with the subject transducer located 10 cm away from a stainless steel plate placed in the focal plane of the transducers. The effect of the stainless steel plate was subtracted from the round trip loss (0.6 dB), so that a direct comparison can be made with the transducers disclosed hereinafter. Under the subject conditions, the ECHO transducer was found to exhibit a round trip loss of 10.0 dB, a 40 dB ring down time of 1.3 microseconds or 4.5 cycles in the ring down time. For these tests, a series inductor/transformer electrical matching network was used. Based on this evaluation, the ECHO transducer is believed to represent the state of the art prior to the inventions disclosed herein, and therefore to be comparable to the best commercially available medical imaging transducers. Other transducers, such as Toray transducer #SN-35M-850, which are believed to utilize $PVF_2$ active elements have also been found to exhibit a 40 dB ring down time of 1.3 microseconds, even though the round trip loss for such transducers has been measured to be in the range of about 19.4 dB. This transducer also exhibited an envelope of oscillations present about 1 microsecond beyond the point of 40 dB decay, which extended for 7 microseconds and was about 34 dB down from the last maximum. Such transducers are thus less preferred for use in medical imaging applications.

SUMMARY OF THE INVENTION

The present invention provides a novel high efficiency large aperture piezoelectric transducer suitable for medical imaging applications exhibiting a 40 dB ring down time of less than 1 microsecond at 4.2 MHz., or less than 3 cycles. This transducer is constructed from a preformed backing material having a flatness of better than 0.0002 inches, a single crystal, lithium niobate active element of ½ wave length thickness, a first matching layer having an impedance of between about $6.8\text{–}7.4\times10^6$ kg/m$^2$ sec and a second matching layer having an impedance of between 1.8 and $2.4\times10^6$ kg/m$^2$ sec. The preferred backing material has an acoustic impedance of less than about 5 which is precast and then carefully lapped to arrive at a surface finish, as measured by a surface finish tester, of within 6 microinches. This backing material is then bonded to the aforementioned single-crystal, lithium niobate active element, and to the preferred first and second matching layers, encased and coated using conventional transducer construction procedures.

It has been recognized that prior art large aperture transducers, which often have had their backings cast against the active element, have tended to deform upon curing, and that disadvantages otherwise inherent in using precast backings can be overcome if such backings are finished to a preselected flatness and to a smooth surface finish, whereby any surface irregularities in the backing material are minimal by comparison to the operating wave length of the transducer. A testing of the preferred medical imaging transducer of the present invention indicates that the physical characteristics achieved in the subject transducer compare favorably to those characteristics predicted for such a transducer using the Stanford theoretical modeling programs discussed above.

The present invention also provides an alternate, dual-power mode transducer, which is particularly adapted for performing the methods of the aforementioned related patent application. The dual mode transducer of the present invention, although exhibiting a longer ring down time, is air backed, capable of delivering sufficient power to underlying body tissue to produce lesions, when desired, but is nonetheless well suited for imaging body tissue, such as the varicose veins described in the above-mentioned related patent application.

Accordingly, a primary object of the present invention is the provision of a novel, large aperture piezoelectric ultrasound transducer exhibiting a 40 dB ring down time of less than 1 microsecond.

Another object of the present invention is the provision of an improved single-crystal lithium niobate ultrasound transducer for use in medical imaging systems.

A further object of the present invention is the provision of an improved lithium niobate transducer which is useful for both lesion producing and imaging applications.

These and other objects of the present invention will become apparent from the following more detailed description.

DESCRIPTION OF THE PREFERRED EMBODIMENTS

While specific examples have been selected for the purposes of illustration in connection with the following description, one of ordinary skill in the art will recognize that various modifications may be made in the materials and methods described hereinafter without departing from the scope of the invention, which is defined more particularly in the appended claims.

Figure 1:
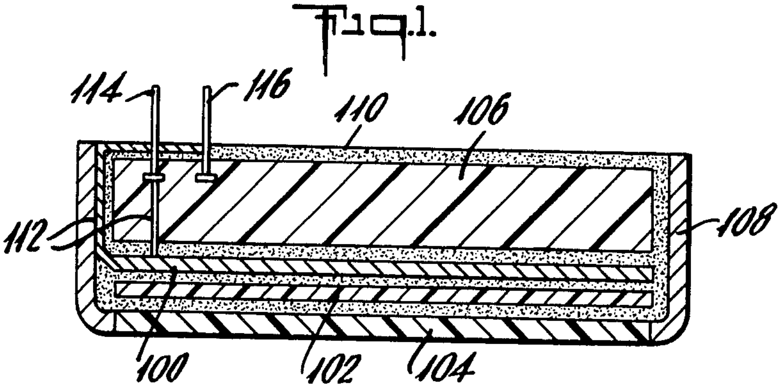
FIG. 1 is a cross-section of the preferred embodiment short ring down time transducer of the present invention wherein the thicknesses of the various layers are exaggerated for the purposes of illustration.

The preferred embodiment short-ring down transducer illustrated in FIG. 1 comprises an active element 100, first and second matching layers 102 and 104, and a backing material 106. These components are bonded to each other with an epoxy bonding material and are encased in a cylindrical stainless steel case 108. The active element 100 is electrically connected through gold foil electrodes to copper electrodes 114 and 116 which are coupled to an appropriate matching network for driving the transducer. The total thickness of the preferred transducer is about ⅞ inch, while the diameter of the transducer is about 3 inches.

The preferred embodiment active element 100 of the transducer of FIG. 1 is a single crystal lithium niobate active element. It is presently preferred to provide such an active element in a thickness equal to ½ of the wave length of the frequency to be used to drive the subject transducer. The velocity of sound through lithium niobate is approximately 7366 meters per second, for a 4.2 MHz transducer in accordance with the preferred embodiment of the present invention, the thickness of the lithium niobate active element should be thus 0.80 mm. The acoustic impedance (Z) of lithium niobate is about 34.6, while the acoustic impedance of water (which roughly corresponds to body tissue) is about 1.5. Therefore, quarter wave matching layers are necessary to efficiently transfer energy from the piezoelectric material to water or body tissue. Without matching layers, about 90% of the energy would be lost. With matching layers, most of the energy is transferred from the transducer into the water. In accordance with the preferred embodiment of the present invention, the first matching layer 102 has an acoustic impedance of between 6.8 and 7.4, and preferably has an impedance of about 7.25. One such material useful for this purpose is Glaskyd 1910 A, which is a plastic sold by American Cyanamid. The thickness of the first matching layer in the preferred embodiment 4.2 MHz transducer is a wafer 0.0060 inches (0.0152 cm) thick. In accordance with the preferred embodiment, the second matching layer has an impedance of between 1.8 and 2.4, and preferably about 2.2. The preferred material for this purpose is a plastic sold under the trade designation ABS by West Side Plastics. The impedance of this material is 2.2 with a thickness of 0.0044 inches in the preferred embodiment. The preferred embodiment backing material is a backing material such as Stycast which is a filled epoxy material sold by Emerson and Cummings, Inc. The backing material 106 is cut from a 3 inch (7.6 cm) O.D. by 12 inch (30.5 cm) long rod which is purchased from Emerson and Cummings in this configuration. The piece originally cut is slightly thicker than 0.750 inches (1.956 cm) so that it can be faced off to 0.750±0.003 inches (±0.0076 cm) on a lathe. Mechanical lapping is then performed using a Strassbaugh lapping machine (model GBK 16 inch precision Polish Master) utilizing several grits of emery paper (e.g. 140, 400, 600) and Slurry diamond compound (S 1313, grade 1, Std. MA). The finished "puck" should meet specifications for parallelism of ±0.0002 inches (±0.0005 cm), flatness of ±0.0002 inches, and a microinch finish of ±4 to 8 microinches ($\pm 1\text{-}2\times 10^{-5}$ cm), preferably about 5 or 6 microinches.

In constructing the preferred transducer, two electrodes are then attached to the lithium niobate wafer before bonding it to the Stycast 265-40 backing puck. The Stycast puck should be milled to provide one notch on the front surface to accommodate electrodes 112 which connect to a face of the active element 100 in a conventional manner. The next step in the process is the bonding of the active element to the stycast backing puck, which is accomplished by attaining a bonding surface temperature of 50° C. cleaning all parts carefully, preparing a bonding agent, such as epoxy DER 332, available from the Dow Chemical Co. and clamping the puck and active element together using a suitable compression jig which will provide uniform overall pressure. The surface of the active element should then be cleaned, using for example epoxy stripper to remove any excess build up of epoxy from the active element-backing bonding operation, whereafter additional gold foil electrodes are soldered in appropriate positions, using care to use a minimum amount of indium solder when attaching these electrodes to prevent cracking or otherwise damaging the crystal or matching layer during bonding. Again using a suitable bonding jig, such as a polytetrafluoroethylene (Teflon®) platform grooved to receive complimental portions of the transducer assembly, the matching layers should be bonded to the active element using a similar bonding operation to that described above.

In accordance with the preferred embodiment of the present invention, materials should be chosen for the matching layers which are machinable, bondable, moldable into useable form and which exhibit the acoustic impedance characteristics discussed above. Such materials should also exhibit a low water sorptivity, on the order of less than or equal to 0.01% water by weight absorption per 24 hours at room temperature. Each of the matching layers should be approximately ¼ wave length thick. The calculated ¼ wavelength thicknesses should be corrected using a skewing factor (such as 1.109 for ABS) to achieve the desired thicknesses referred to above.

The matching layers may be bonded to the active layer (or to each other) again using a suitable epoxy such as DER 332. The matching layers should be positioned in their proper orientation for bonding, care should be taken to ensure that no air is trapped between the matching layers, and the composite should be bonded, one matching layer at a time, under pressure, preferably with the use of a flat stainless steel disk to ensure that the matching layers will not deform during the bonding and curing process. The composite unit may then be assembled such that gold foil electrodes 112 are connected to copper electrodes 114 and 116 which extend out of the back of the unit. The composite assembly is then encased in a stainless steel housing ring which is preferably 3.375 inches (8.57 cm) O.D. and 3.150 inch (8.0 cm) I.D. by ⅞ inch (2.22 cm) thick. A suitable ground wire 2 inches (5.08 cm) long is soldered into place with silver solder, and the transducer is oriented so that the gold foil electrodes 112 will be disposed adjacent suitable notches which are formed along the interior surface of stainless steel case 108. The unit may then be assembled ensuring that there is no continuity between the ring and electrodes, and the central slot and periphery of the transducer should be filled with an epoxy, such as Hardman gap filling epoxy and/or the DER 332 epoxy referred to above.

The back of the transducer is then filled across its entire surface with a two ton crystal clear epoxy, such as that sold by Devco which is provided with a colorant addition (such as Harshaw colorants), which is then allowed to cure. The final finished transducer is paralene coated for the purpose of protecting the transducer from the operating environment.

Figure 2:
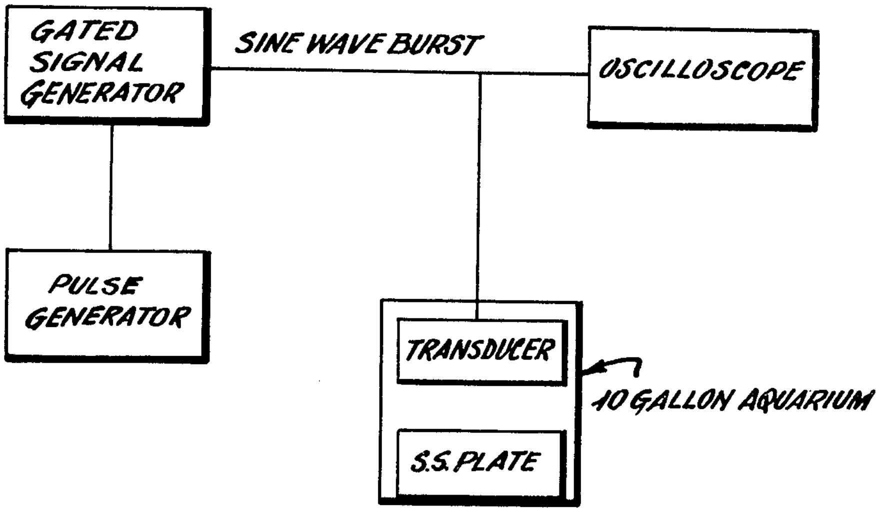
FIG. 2 is a schematic of the test fixture used to determine the round trip loss and ring down time of the transducers disclosed herein.
Figure 3:
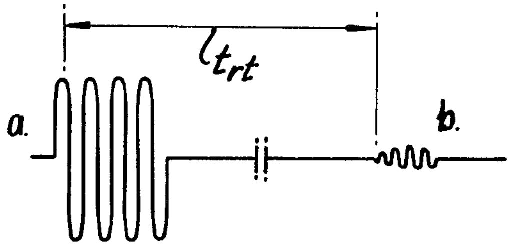
FIG. 3 is a diagrammatic illustration of the 10 cycle sine wave burst provided to the transducer during testing, and the receipt by the transducer of the return pulse (b) reflected from the stainless steel plate after time $t_{rt}$.
Figure 4:
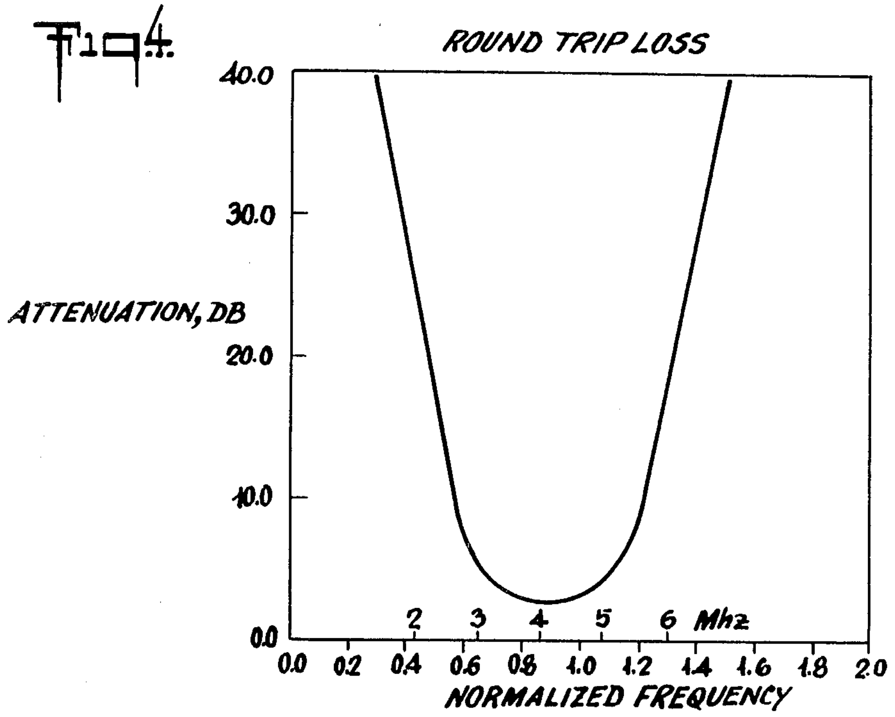
FIG. 4 is round trip loss graph of attenuation vs. frequency for the preferred embodiment transducer of the present invention showing theoretical and actual values for the preferred embodiment short ring down time transducer of the present invention.

A transducer as described above was tested in a water path as shown in FIG. 2. The transducer was excited by a ten cycle tone burst similar to the tone burst illustrated in FIG. 3*a* which was reflected off a finely polished stainless steel plate. Round trip loss and ring down time were estimated using the return pulse illustrated in FIG. 3*b*. The subject transducer was found to have a 40 dB ringdown time at 4.2 MHz of 0.7 microseconds, and a round trip loss of 6.8 dB, as indicated by the experimentally derived data points ("+") of FIG. 4. This transducer had a ReZe=27.1 ohms, and an ImZe of 25.1 ohms. After 18 months testing in a normal operating environment, no detectable changes in the characteristics of the transducer have been detected. Accordingly, the transducer takes advantage of the uniform crystalline properties of lithium niobate, as well as the high electromechanical conversion, low dielectric constant, high sonic velocities, and high polarization temperatures to produce a superior transducer. Those of ordinary skill in the art will recognize that the subject transducer has a high Curie temperature (approximately 1200° C.) which makes the transducer fairly temperature insensitive and aids in the maintenance of polarization of the transducer during its use.

Figure 5:
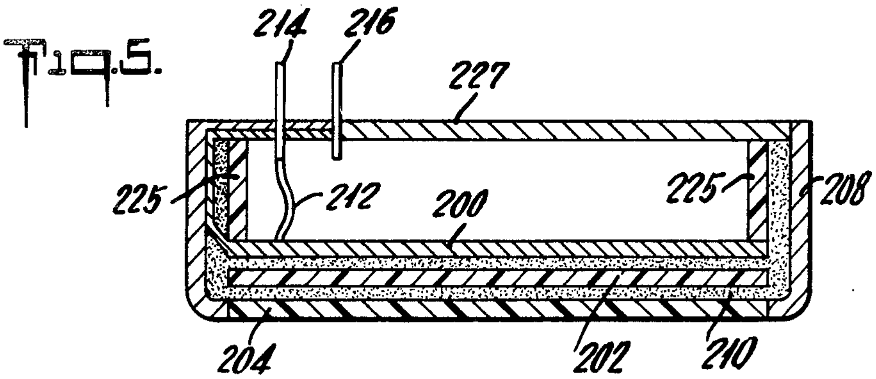
FIG. 5 is a cross-section of the air-backed preferred embodiment dual-power transducer of the present invention wherein the thicknesses of the various layers are exaggerated for purposes of illustration.
Figure 6:
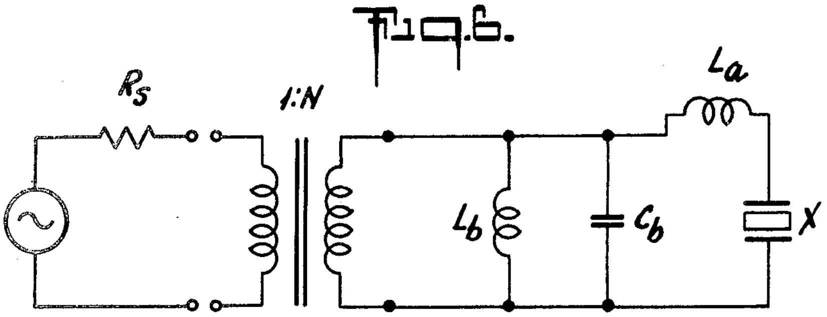
FIG. 6 is a schematic of the preferred embodiment matching network for use with the transducer of FIG. 5.

In accordance with an alternate embodiment of the present invention, a transducer is provided which is uniquely suited for use in performing the methods disclosed in the aforementioned related patent application of David Vilkomerson. This preferred embodiment transducer is illustrated in FIG. 5, with corresponding components being labeled similarly to the components of the transducer of FIG. 1, except in the 200 series, unless otherwise noted hereinafter. Unlike the transducer of FIG. 1, the transducer of FIG. 5 is air backed, thereby increasing the efficiency of the transducer, albeit at the expense of somewhat greater ring down times. By providing a high efficiency, air backed transducer, the subject transducer may be operated at high power levels without overheating and while achieving very high efficiencies (very low round trip losses). In accordance with this embodiment, the matching layer impedance is also changed to increase efficiency of the device. The first matching layer is selected to have impedance of between about 2 and 2.5, preferably about 2.25. This matching layer is preferably composed of ABS which may be purchased from West Lake Plastics. The second matching layer has an impedance of between about 6.5 and 7, preferably about 6.8 composed of the material MF114 which is available from Emerson-Cumming. The preferred thickness of the first matching layer is about 0.0045 inches (0.0114 cm), while the thickness of the second matching layer for this embodiment is about 0.0042 inch (0.0107 cm). When driven at frequencies of 3.6 MHz with different electrical matching networks, the round trip loss for this transducer ranged from 1.0 to 4.0 dB while the ringdown times ranged from 10 to 1.2, microseconds i.e. from 36 cycles to 4.3 cycles. In FIG. 6, a schematic is illustrated of the various matching networks utilized to obtain the aforementioned round trip loss and ring down times. When the preferred embodiment dual-power transducer is to be used for tissue imaging, it is desired to utilize a matching network which will achieve a 40 dB ring down time in the order of 1.2 microseconds and, under such circumstances, a round trip loss of 4.0 dB. When the transducer is used in its high power mode, as for example to produce tissue lesions, very low round trip losses are preferred and much higher ring down times are acceptable. Accordingly, it is preferred to utilize a different matching network to drive the transducer in the high power mode for the purpose of producing tissue lesions.

As seen in FIG. 6, each of the preferred matching networks couples a series inductor $L_a$ to the transducer X. The circuit is powered by a transformer, the primary to secondary winding ratio of which is indicated as 1:N in FIG. 6. This transformer is connected to a suitable power source 400. The resistor $R_s$ is the source impedance. When the matching network illustrated in FIG. 6 is to be used to obtain optimal ring down times, the preferred matching network should further include parallel inducter $L_b$ and parallel capacitor $C_b$, which generally function to reduce ring down time. The preferred matching network resulting in short ring down times comprises components having the following specifications:

| | |
|---|---|
| $L_a$ | $1.29 \times 10^{-6}$ H |
| $L_b$ | $2.03 \times 10^{-6}$ H |
| $C_b$ | $1.28 \times 10^{-9}$ F |
| 1:N | 1:2.5 |

When the machining network of FIG. 6 is to be utilized in the low round trip loss (high ring down) high power mode, the transducer is to be powered with a continuous wave, such as sign wave and parallel inductor $L_b$ and parallel capacitor $C_b$ should be eliminated from the matching network. The specifications for the remaining components are preferably as follows:

| | |
|---|---|
| $L_a$ | approximately $2.0 \times 10^{-6}$ H |
| 1:N | 1:1.5 |

Under certain circumstances it may be preferred to optimize both round trip loss and ring down time so that the same matching network may be used to both image and produce lesions when used with the preferred embodiment transducer of the present invention. A matching network having components with the following specifications has been found suitable to achieve a round trip loss of 2.8 dB and a 40 dB ring down time of 1.6 microseconds. Components for such a matching network should have the following specifications:

| | |
|---|---|
| $L_a$ | $1.23 \times 10^{-6}$ H |
| $L_b$ | $2.03 \times 10^{-6}$ H |
| $C_b$ | $1.28 \times 10^{-3}$ F |
| 1:N | 1:1.5 |

In utilizing the preferred embodiment dual power mode transducer in performing the methods of the aforementioned related patent application, one of ordinary skill in the art will recognize that either separate matching networks may be provided which are alternately switched for use with the preferred embodiment dual-power transducer, or alternatively, when the optimal alternate matching network is utilized, the amplitude of signal provided to the transducer may be appropriately adjusted through the use of a selectively variable resistance in additional to or in place of $R_s$. For purposes of convenience, it is presently preferred to provide separate matching networks, the high power network of which is optimized for low round trip loss, and the low-power imaging network of which optimizes the transducer with respect to ring down time.

The dual-power transducer illustrated in FIG. 5 is constructed in a manner similar to that hereinabove described for the short-ring down preferred embodiment imaging transducer. Construction of the dual-power transducer differs, however, in that a plastic cylinder 225 is bonded to the active element in place of the stycast backing described above. Cylinder 225 is glued to an outer side annular portion of the active element, leaving the bulk of the surface area of the active element entirely airbacked. This procedure is conducted by placing the active element on a support surface, gluing its edge, applying the plastic cylinder, which is approximately 0.05 inches thick on the active element under pressure to accomplish bonding with a suitable epoxy, such as the two-ton epoxy described above. Following bonding, excess epoxy is removed using epoxy stripper, whereupon a tightly fit Teflon ® puck is inserted into the interior of the plastic cylinder to prevent warpage during the remaining portion of the construction operation. Bonding of the matching layers and assembly of the electrodes proceeds in the same manner as described with respect to the embodiment of FIG. 1, except that the Teflon ® puck is removed immediately prior to the finishing operation, and a plastic backing 227 is placed over the back portion of the cylinder and bonded to the back of the case to enclose the air space. The final operation in the construction of the preferred dual-power transducer is then connection of the gold foil electrodes to the copper pins, following the a coding with a sealer such as two-ton epoxy or Tracon ® 2151 epoxy.

One of ordinary skill in the art will recognize that the disclosed dual-power transducer should be operated at a frequency and amplitude suitable for imaging tissues to be lesioned. Those of ordinary skill in the art will also recognize that at the higher power level mode the amplitude of signals delivered to the transducer should be sufficient to raise the temperature of the tissue to be lesioned by at least 10° C., and preferably 20+° C., or to about 45° to 55° C. Those of ordinary skill in this art will recognize that the level of power at which the transducer should be driven will be dependent upon many factors including the nature of the tissue to be lesioned, the depth of that tissue, the focal length of associated acoustic lens, the desired length of power application, and other factors which make precise prediction of the power required to be delivered to a given tissue portion difficult. Nonetheless, using the preferred embodiment transducer and matching network of the present invention, it is anticipated that less than 200 watts of power need be provided to the transducer in order to effect the lesion of a typical varicose vein to be treated in accordance with the method of the aforementioned related patent application of David Vilkomerson. As seen from the above description, the present invention thus provides a simple, highly efficient air backed transducer, which is capable of functioning effectively in a low-power imaging mode as well as a high-power lesion producing mode.

I claim:

1. A high efficiency, piezoelectric transducer suitable for medical imaging applications, having a 40 dB ring down time of less than 3 cycles at an emission frequency suitable for medical imaging use, comprising:

(a) a preformed backing material having a mating surface with a flatness of at least 0.0002 inches;

(b) a single crystal, lithium niobate active element bonded to said mating surface of said backing material;

(c) a first matching layer bonded to said active element having an acoustic impedance of between $6.8\times16^6$ Kg/m$^2$ sec and $7.4\times10^6$ Kg/m$^2$ sec; and (d) a second matching layer bonded to said first matching layer having an impedance of between $1.8\times10^6$ Kg/m$^2$ sec and $2.4\times10^6$ Kg/m$^2$ sec.

2. The invention of claim 1 wherein said preformed backing material comprises a surface contiguous to said active element exhibiting a microinch finish of between about ±4–8 microinches.

3. The invention of claim 2 wherein said finish is a 5–6 microinch finish.

4. The invention of claim 2 wherein said preformed backing material is formed into a backing puck having a parallelism of at least 0.0002".

5. The invention of claim 1 wherein said first matching layer has an impedance of about $7.25\times10^6$ Kg/m$^2$ sec.

6. The invention of claim 1 wherein said second matching layer has an impedance of about $2.2\times10^6$ Kg/m$^2$ sec.

7. The inventon of claim 1 wherein said transducer has a 40 dB ring down time at 4.2 MHz of about 0.7 microseconds.

8. The invention of claim 1 wherein said transducer is designed to operate at frequencies between 3 and 5.5 MHz, and wherein said single crystal lithium niobate active layer has a thickness of about 0.8 mm.

9. The invention of claim 8 wherein said first matching layer has a thickness of about 0.006 inches.

10. The invention of claim 8 wherein the thickness of said second matching layer is about 0.0044 inches.

11. The invention of claim 1 wherein said transducer has an acoustic aperture of greater than 2.5 inches.

12. A dual-power, ultrasonic transducer for selectively imaging or scarring body tissues, comprising:

(a) an air backed, piezoelectric active element;

(b) matching layer means for acoustically matching said active element to said tissues;

(c) a power source for providing a continuous wave signal of preselected frequency and amplitude to said transducer;

(d) a first matching network for matching said continuous wave signal to said transducer to provide a transducer 40 dB ring down of less than about 5 cycles, whereby said transducer is suitable for use in a tissue imaging system;

(e) a second matching network for optimizing the efficiency of said transducer to provide a round trip loss of less than about 2 dB to said transducer; and (f) switching means for selectively coupling said first or said second matching network between said power source and said active element for selectively imaging or scarring said body tissues.

13. The invention of claim 12 wherein said air backed piezoelectric active element is a single crystal lithium niobate element.

14. The invention of claim 12 wherein said lithium niobate active element has a thickness equal to ½ wavelength of said operating frequency.

15. The invention of claim 12 wherein said air backed piezoelectric active element comprises a single crystal lithium niobate active element bonded at its periphery to an annular supporting cylinder.

16. The invention of claim 12 wherein said matching layer means comprises first and second matching layers.

17. The invention of claim 16 wherein said first matching layer comprises a material having an acoustic impedance of between about $2.0–2.5\times10^6$ Kg/m$^2$ sec.

18. The invention of claim 17 wherein said first matching layer has an acoustic impedance of about $2.25\times10^6$ Kg/m$^2$ sec.

19. The invention of claim 16 wherein said second matching layer is composed of a material having an acoustic impedance of between about 6.5 and $7.0\times10^6$ Kg/m$^2$ sec.

20. The invention of claim 19 wherein said second matching layer has an acoustic impedance of about $6.8\times10^6$ Kg/m$^2$ sec.

21. The invention of claim 20 wherein the thickness of said single crystal lithium niobate active element is about 0.8 mm.

* * * * *